United States Patent
Brüchner et al.

(10) Patent No.: US 10,618,872 B2
(45) Date of Patent: Apr. 14, 2020

(54) PROCESS FOR PREPARING 3-CHLORO-2-VINYLPHENYLSULFONATES

(71) Applicant: BAYER CROPSCIENCE AKTIENGESELLSCHAFT, Monheim am Rhein (DE)

(72) Inventors: Peter Brüchner, Krefeld (DE); Thomas Himmler, Odenthal (DE); Sergii Pazenok, Solingen (DE); Mark James Ford, Wiesbaden-Breckenheim (DE)

(73) Assignee: Bayer CropScience Aktiengesellschaft, Monheim am Rhein (DE)

( * ) Notice: Subject to any disclaimer, the term of this patent is extended or adjusted under 35 U.S.C. 154(b) by 0 days.

(21) Appl. No.: 15/554,271

(22) PCT Filed: Feb. 29, 2016

(86) PCT No.: PCT/EP2016/054189
§ 371 (c)(1),
(2) Date: Aug. 29, 2017

(87) PCT Pub. No.: WO2016/139161
PCT Pub. Date: Sep. 9, 2016

(65) Prior Publication Data
US 2018/0079717 A1  Mar. 22, 2018

(30) Foreign Application Priority Data
Mar. 5, 2015 (EP) .................................... 15157832

(51) Int. Cl.
*C07C 303/28* (2006.01)
*C07C 39/24* (2006.01)
*C07C 309/66* (2006.01)
*C07C 37/20* (2006.01)
*C07C 45/43* (2006.01)
*C07C 67/14* (2006.01)
*C07C 67/287* (2006.01)
*C07C 68/02* (2006.01)
*C07C 68/06* (2006.01)
*C07C 69/63* (2006.01)
*C07C 69/96* (2006.01)
*C07C 37/00* (2006.01)

(52) U.S. Cl.
CPC .......... *C07C 303/28* (2013.01); *C07C 37/002* (2013.01); *C07C 37/20* (2013.01); *C07C 39/245* (2013.01); *C07C 45/43* (2013.01); *C07C 67/14* (2013.01); *C07C 67/287* (2013.01); *C07C 68/02* (2013.01); *C07C 68/06* (2013.01); *C07C 69/63* (2013.01); *C07C 69/96* (2013.01); *C07C 309/66* (2013.01)

(58) Field of Classification Search
None
See application file for complete search history.

(56) References Cited

U.S. PATENT DOCUMENTS

| | | | |
|---|---|---|---|
| 5,124,460 A | 6/1992 | Humphrey et al. | |
| 5,817,890 A | 10/1998 | Duhamel et al. | |
| 6,057,352 A * | 5/2000 | Brown .................. | A01N 43/653 514/384 |
| 2011/0237575 A1 | 9/2011 | Shipps et al. | |
| 2014/0057945 A1 | 2/2014 | Cristau et al. | |
| 2016/0135461 A1 | 5/2016 | Hillebrand et al. | |

FOREIGN PATENT DOCUMENTS

| | | |
|---|---|---|
| EP | 0 511 036 A1 | 10/1992 |
| EP | 3013821 A1 | 5/2016 |
| JP | H5-140137 A | 6/1993 |
| WO | 2001083417 A1 | 11/2001 |
| WO | 2011076699 A1 | 6/2011 |
| WO | 2014/206896 A1 | 12/2014 |

OTHER PUBLICATIONS

Dale et al. "Syntheses and Properties of Vinylphenols", Journal of American Chemical Society (JACS), Jul. 20, 1958, vol. 80, pp. 3645-3649.
Kumar et al., "Neutral Ionic Liquid [hmim]Br as a Green Reagent and Solvent for the Mild and Efficient Dehydration of Benzyl Alcohols into (E)-Arylalkenes Under Microwave Irradiation[‡]", Neutral Ionic Liquid, Eur. J. Org. Chem. (2008), pp. 5577-5582.
Kamogawa et al., Unusual Disproportionation Encountered in the Alumina-Catalyzed Dehydration of 4-(L-Hydroxyethyl)Phenols, (1980), Chemistry Letters, pp. 793-794.
International Search Report of PCT/EP2016/054189 dated Apr. 29, 2016.
Brooks, Lester. A., "Preparation of Substituted Styrenes," Journal of the American Chemical Society, 1944, vol. 66, No. 8, pp. 1295-1297.

* cited by examiner

*Primary Examiner* — Po-Chih Chen
(74) *Attorney, Agent, or Firm* — McBee Moore & Vanik IP, LLC

(57) ABSTRACT

The present invention relates to a new process for preparing 3-chloro-2-vinylphenylsulfonate derivatives.

15 Claims, No Drawings

PROCESS FOR PREPARING 3-CHLORO-2-VINYLPHENYLSULFONATES

CROSS REFERENCE TO RELATED APPLICATIONS

This application is a § 371 National State Application of PCT/EP2016/054189, filed Feb. 29, 2016, which claims priority to European Application No. 15157832.5 filed Mar. 5, 2015.

BACKGROUND OF THE INVENTION

Field of the Invention

The present invention relates to a new process for preparing 3-chloro-2-vinylphenylsulfonate derivatives.

3-Chloro-2-vinylphenylsulfonates of the general formula (I) are important intermediates for the synthesis of agrochemicals. Especially the 3-chloro-2-vinylphenyl-methanesulfonate is a valuable precursors of active fungicidal ingredients (e.g. WO 2011/076699 or WO 2014/206896).

Description of Related Art

A typical synthesis of 3-chloro-2-vinylphenylsulfonates of the general formula (I) is the reaction of 3-chloro-2-vinylphenol with an aryl- or alkylsulfochloride. The synthesis of the starting material 3-chloro-2-vinylphenol is already known (EP 0511036 B1): Starting from tetrachlorocyclohexanone, what has to be prepared by chlorination of cyclohexanone, upon addition of vinylmagnesium bromide the desired vinyltetetrachlorocyclohexanol was formed and further transformed into the vinyl-2-oxa-7-bicycloheptane. Its opening upon reflux in N,N-dimethylformamide (DMF) gave finally 3-chloro-2-vinylphenol in a low total yield. Thus, this process is not suitable for commercial application. Especially the atom economy of this process is insufficient, since from 4 chlorine atoms presented in the starting tetrachlorocyclohexanone only one remains in the molecule.

Simple unprotected vinylphenols are highly prone to polymerization and further side reactions (*Chemistry Letters* 1980, 7, 793). Typical procedures for synthesis of these compounds include dehydration of hydroxyethyl-substituted phenyls, promoted by $Al_2O_3$, $KHSO_4$ or $H_2SO_4$ (*Journal of the American Chemical Society*, 1958, 80, 3645), giving the product usually in low yield and with significant amounts of side products. A single example of a para-vinyl-phenol derivative was obtained in an ionic liquid under Microwave conditions in 56% yield (*Eur. J. Org. Chem.* 2008, 33, 5577), which is not feasible for industrial scale. In addition, synthesis of unprotected ortho-vinyl-phenols by elimination has not been described at all in literature. Therefore, we were surprised to find that the elimination of unprotected metachloro-ortho-(1-hydroxyethyl)phenol proceeds to the corresponding ortho-vinylphenol derivative in good yield.

SUMMARY

In the light of the prior art described above, it is an object of the present invention to provide a process that does not have the aforementioned disadvantages and hence gives a route to 3-chloro-2-vinylphenylsulfonate derivatives in high yields.

The object described above was achieved by a process for preparing 3-chloro-2-vinylphenylsulfonates of the formula (I)

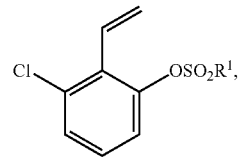

(I)

in which
$R^1$ represents $C_1$-$C_6$-alkyl, phenyl, 4-methylphenyl or benzyl,
characterized in that in step (A) 3-chloro-2-methylphenol of the formula (II)

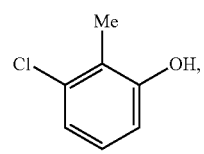

(II)

is reacted with a compound of the general formula (III),

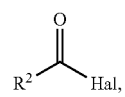

(III)

in which
Hal represents F, Cl, or Br and
$R^2$ represents F, Cl, Br, $F_3C$, $F_2HC$, $Cl_3C$, $Cl_2HC$, $ClH_2C$ or $Cl_3CO$,
or is reacted
with an acid derivative of the general formula (IV),

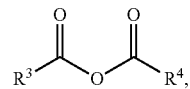

(IV)

in which
$R^3$ and $R^4$ independently from each other represent $F_3C$, $F_2HC$, $Cl_3C$, $Cl_2HC$, $ClH_2C$
or is reacted
with triphosgen
in the presence of a base and a solvent
to form the compound of the general formula (V)

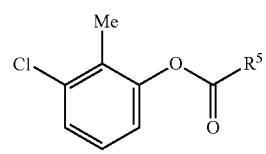

(V)

in which

R⁵ represents F, Cl, CCl₃, CHCl₂, CH₂Cl, CF₃, CHF₂ or 3-chloro-2-methylphenoxy and that in step (B) compounds of the formula (V) are reacted with a chlorinating agent to produce compounds of the formula (VI)

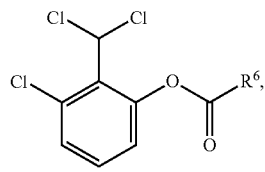

(VI)

in which

R⁶ represents F, Cl, CCl₃, CHCl₂, CH₂Cl, CF₃, CHF₂ or 3-chloro-2-(dichloromethyl)phenoxy and that in step (C) the compound of general formula (VI) is reacted to 2-chloro-6-hydroxybenzaldehyde (VII)

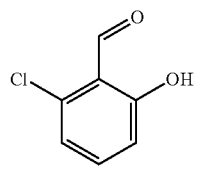

(VII)

under acidic conditions or at elevated temperature in water and that in step (D) the compound of the formula (VII) or its alkaline or alkaline earth metal salt is reacted in the presence of a solvent with a compound of the formula (VIII)

Me-Q (VIII), in which

Q represents Li, Na, K, MgCl, MgBr or, MgI to produce 3-chloro-2-(1-hydroxyethyl)phenol (IX)

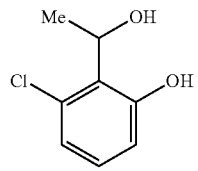

(IX)

and that in step (E) 3-chloro-2-vinylphenylsulfonate of the formula (I) is formed by reacting compound of the formula (IX) in the presence of a base with compound of the general formula (X)

R¹—SO₂—W (X), in which

W represents F, Cl, Br or OSO₂R¹ and

R¹ has the meanings disclosed above.

DETAILED DESCRIPTION OF A PREFERRED EMBODIMENT

Preferred is a process according to the present invention, where the radicals in formula (I) to (X) are defined as follows:

R¹ represents methyl, ethyl, n-propyl, i-propyl, n-butyl, phenyl, 4-methylphenyl or benzyl;

R² represents F, Cl, F₃C, F₂HC, Cl₃C, Cl₂HC, ClH₂C or Cl₃CO,

R³ and R⁴ independently from each other represent F₃C, F₂HC, Cl₃C, Cl₂HC, ClH₂C

R⁵ represents F, Cl, CCl₃, CHCl₂, CH₂Cl, CF₃, CHF₂ or 3-chloro-2-methylphenoxy;

R⁶ represents F, Cl, CCl₃, CHCl₂, CH₂Cl, CF₃, CHF₂ or 3-chloro-2-(dichloromethyl) phenoxy;

W represents F, Cl or OSO₂R¹;

Q represents Na, K, MgCl or MgBr.

Especially preferred is a process according to the present invention, where the radicals in formula (I) to (X) are defined as follows:

R¹ represents methyl, ethyl, n-propyl, phenyl, 4-methylphenyl;

R² represents F, Cl, F₃C, F₂HC, Cl₃C, Cl₂HC, ClH₂C or Cl₃CO,

R³ and R⁴ independently from each other represent F₃C, Cl₃C, Cl₂HC, ClH₂C;

R⁵ represents F, Cl, CCl₃, CHCl₂, CH₂Cl, CF₃, F₂HC or 3-chloro-2-methylphenoxy;

R⁶ represents F, Cl, CCl₃, CHCl₂, CH₂Cl, CF₃, F₂HC or 3-chloro-2-(dichloro)methylphenoxy;

W represents F, Cl or OSO₂R¹;

Q represents Na, K, MgCl or MgBr.

Most preferred is a process according to the present invention, where the radicals in formula (I) to (X) are defined as follows:

R¹ represents methyl or 4-methylphenyl;

R² represents F, Cl, F₃C or Cl₃CO;

R³ and R⁴ independently from each other represent F₃C or Cl₃C,

R⁵ represents F, Cl, CCl₃, F₃C or 3-chloro-2-methylphenoxy;

R⁶ represents F, Cl, CCl₃, F₃C or 3-chloro-2-(dichloro)methylphenoxy;

W represents F, Cl or OSO₂R¹;

Q represents MgCl or MgBr.

A further aspect of the present invention are compounds of the formula (V)

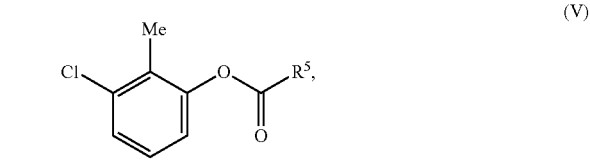

(V)

in which

R⁵ represents F, Cl, CCl₃, CHCl₂, CH₂Cl, CF₃, CHF₂ or 3-chloro-2-methylphenoxy.

Preferred are compounds of the formula (V), in which

R⁵ represents F, Cl, CCl₃, CHCl₂, CH₂Cl or 3-chloro-2-methylphenoxy.

Especially preferred are compounds of the formula (V), in which

R⁵ represents Cl, CCl₃, or 3-chloro-2-methylphenoxy.

A further aspect of the present invention are compounds of the formula (VI)

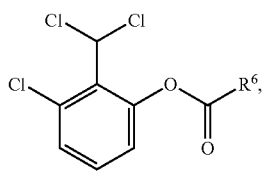
(VI)

in which

R⁶ represents F, Cl, CCl₃, CHCl₂, CH₂Cl, CF₃, CHF₂, or 3-chloro-2-(dichloromethyl)phenoxy.

Preferred are compounds of the formula (VI), in which

R⁶ represents F, Cl, CCl₃, CHCl₂, CH₂Cl or 3-chloro-2-(dichloromethyl)phenoxy.

Especially preferred are compounds of the formula (VI), in which

R⁶ represents Cl, CCl₃ or 3-chloro-2-(dichloromethyl)phenoxy.

A further aspect of the present invention is 3-chloro-2-(1-hydroxyethyl)phenol (IX)

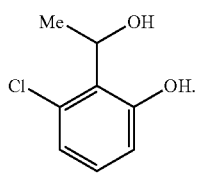
(IX)

General Definitions

In the context of the present invention, the term "halogen" (Hal), unless defined differently, comprises those elements which are selected from the group comprising fluorine, chlorine, bromine and iodine, preferably fluorine, chlorine and bromine, more preferably fluorine and chlorine.

Alkyl groups in the context of the present invention, unless defined differently, are linear or branched saturated hydrocarbyl groups. The definition $C_1$-$C_6$-alkyl encompasses the widest range defined herein for an alkyl group. Specifically, this definition encompasses, for example, the meanings of methyl, ethyl, n-, isopropyl, n-, iso-, sec- and t-butyl, n-pentyl, n-hexyl, 1,3-dimethylbutyl, 3,3-dimethylbutyl.

Process Description

The process of the present invention is illustrated in Scheme 1:

Scheme 1:

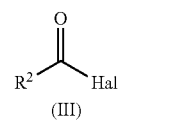
(III)

or

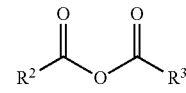
(IV)

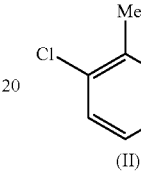
(II)

or triphosgen
→
step A

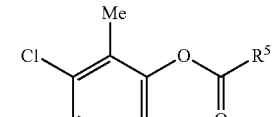
(V)
→ step B

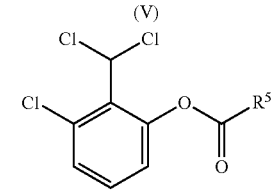
(VI)
→ step C

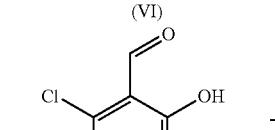
(VII)

Me—Q
(VIII)
→ step D

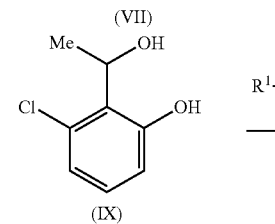
(IX)

R¹—SO₂—W
(X)
→ step E

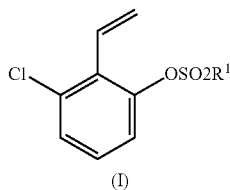
(I)

Step A:

In step (A) of the present invention the phenol (II) is reacted with compounds of the general formula (III) or compounds of the general formula (IV) or triphosgen in the presence of a base and a solvent to yield compounds of the general formula (V).

The 2-methyl-3-chlorophenol (II) is known and can be prepared from 2,6-dichlorophenol, which is a cheap starting material, according to WO 2001/083417.

Most preferred compounds of the formula (III) to prepare the compounds of the formula (V) are dichloroacetylchloride, trichlorocetylchloride, phosgene, diphosgene, and difluorophosgen. It is also possible to generate compounds of general formula (V) using compounds of the general formula (IV), most preferably dichloraceticacid anhydride, trichloroaceticacid anhydride or trifluoroaceticacid anhydride, or to use triphosgen. These compounds are commercially available.

Step (A) according to the invention is effected at temperatures of 0° C. to +120° C., preferably at temperatures of 0° C. to +100° C., more preferably at 20° C. to +60° C.

The reaction of step (A) is performed under normal pressure, but can also be performed under reduced or elevated pressure.

Step (A) is performed in the presence of a base. Typical bases are trialkylamines, pyridine, alkylpyridines, or diazabicycloundecen (DBU). Alkylpyridines are the preferred bases. Most preferred are 3-methylpyridine and 2-methyl-5-ethylpyridine.

The amount of base in step (A) is 1 to 2 mol, preferred 1 to 1.5 mol, of the base for 1 mol of compound of the formula (II).

The reaction time is not critical and may, according to the batch size and temperature, be selected within a range between a few minutes and several hours.

In step (A) 1 to 2 mol, preferably 1 to 1.5 mol, most preferably 1 to 1.2 mol of the acid derivatives of the formula (III) is reacted with 1 mol of compound of the formula (II).

Suitable solvents are, for example, aliphatic, alicyclic or aromatic hydrocarbons, for example petroleum ether, n-hexane, n-heptane, cyclohexane, methylcyclohexane (MCH), toluene, xylene or decalin; halogenated hydrocarbons, for example chlorobenzene, dichlorobenzene, dichloromethane, chloroform, tetrachloromethane, dichloroethane or trichloroethane; ethers such as diethyl ether, diisopropyl ether, methyl tert-butyl ether (MTBE), methyl tert-amyl ether, dioxane, tetrahydrofuran (THF), 1,2-dimethoxyethane, 1,2-diethoxyethane or anisole; nitriles such as acetonitrile, propionitrile, n- or isobutyronitrile or benzonitrile; amides such as N,N-dimethylformamide (DMF), N,N-dimethylacetamide (DMAC), N-methylformanilide, N-methylpyrrolidone (NMP) or hexamethylphosphoramide; sulfoxides such as dimethyl sulfoxide (DMSO) or sulfones such as sulfolane, or mixtures of these solvents. Preference is given, for example, to THF, acetonitrile, ethers, toluene, xylene, chlorobenzene, n-hexane, cyclohexane or MCH, or mixtures of these solvents; and particular preference is given to dichloromethane, toluene, chlorobenzene and dichloromethane, or mixtures of these solvents.

The compounds of the formula (V) formed can be used for the next step without prior workup.

Alternatively, the compounds of the formula (V) can be isolated by suitable workup steps, characterized and optionally further purified.

Step B

In step (B) compounds of the formula (V) are reacted with a chlorinating agent to produce compounds of the formula (VI).

For step (B) a solvent can be used. Suitable solvents are, for example, aliphatic, alicyclic or aromatic hydrocarbons, for example petroleum ether, n-hexane, n-heptane, cyclohexane, MCH, toluene, ortho-xylene, meta-xylene, para-xylene or decalin, and halogenated hydrocarbons, for example chlorobenzene, 1,2-dichlorobenzene, dichloromethane, chloroform, tetrachloromethane, dichloroethane or trichloroethane, ethers such as diethyl ether, diisopropyl ether, MTBE, methyl tert-amyl ether, dioxane, THF, 1,2-dimethoxyethane, 1,2-diethoxyethane or anisole; nitriles such as acetonitrile, propionitrile, n- or isobutyronitrile or benzonitrile; or mixtures of solvents.

It is also possible to perform step (B) without a solvent.

Preference is given, for example, to n-hexane, n-heptane, cyclohexane, MCH, toluene, ortho-xylene, meta-xylene, para-xylene or decalin, and halogenated hydrocarbons, for example chlorobenzene, 1,2-dichlorobenzene, dichloromethane, chloroform, tetrachloromethane, dichloroethane or trichloroethane, or mixtures of these solvents. Particular preference is given to chlorobenzene, 1,2-dichlorobenzene, dichloromethane, chloroform, tetrachloromethane, dichloroethane or trichloroethane, or mixtures of these solvents.

The chlorination reaction of step (B) can be performed with chlorinating agents like elemental chlorine ($Cl_2$) or sulfurylchloride ($SO_2Cl_2$). The use of $Cl_2$ is preferred.

For the chlorination reaction of step (B) the chlorinating agent is used in stoichiometric amounts or in access. If an access of the chlorinating agent is used no over chlorination to trichloromethyl substituted compounds is observed.

Step (B) of the present invention can be performed at different temperatures, for example in a range between 0° C. and 200° C. It is preferred to perform the reaction in a range between 50° C. and 150° C.

The chlorination of step (B) of the present invention can be accelerated by the addition of so called radical starters, for example azo-bis(isobutyronitrile) (AIBN), di-(tert.butyl)-peroxide, or dibenzoylperoxide, or by irradiating the reaction mixture with a UV-lamp. It is preferred to accelerate the reaction by irradiating the reaction mixture with a UV-lamp.

The reaction of step (B) is done under normal pressure, but can also be performed under reduced or elevated pressure.

Step C

In step (C) 3-chloro-2-(dichloromethyl) phenyloxy derivatives of the formula (VI) are transformed into 2-chloro-6-hydroxybenzaldehyde of the formula (VII) under acidic conditions or at elevated temperature in water.

Acidic Conditions

Suitable acids are mineral acids, for example $H_2SO_4$, HCl, HF, HBr, HI, $H_3PO_4$ or organic acids, for example $CH_3COOH$, $CF_3COOH$, p-toluenesulfonic acid, methanesulfonic acid, trifluoromethanesulfonic acid. Preference is given to HCOOH, $CH_3COOH$, $H_2SO_4$, and HCl. Acids could be used in a pure form or as a water solution.

In step (C) 0.1 mol to 20 mol, preferably 0.3 to 15 mol of the acid for 1 mol of compounds of the formula (VI) is used. The reaction is effected at temperatures of 50° C. to +120° C., preferably at temperatures of 60° C. to +100° C., more preferably at 70° C. to +100° C. The reaction of step (C) is performed under normal or elevated pressure.

Additional organic solvent could be used.

Elevated Temperature in Water

It is also possible to perform the reaction without any acid only in water under elevated temperature. The reaction in water is effected at temperatures of 80 to +140° C. To perform the reaction in water at a temperature above 100° C. additional pressure up to 10-20 bar is needed.

Additional organic solvent could be used.

Suitable solvents for step (C) are, for example, aliphatic, alicyclic or aromatic hydrocarbons, for example petroleum ether, n-hexane, n-heptane, cyclohexane, MCH, toluene, xylene or decalin, and halogenated hydrocarbons, for example chlorobenzene, dichlorobenzene, dichloromethane, chloroform, tetrachloromethane, dichloroethane or trichloroethane, ethers such as diethyl ether, diisopropyl ether, MTBE, methyl tert-amyl ether, dioxane, THF, 1,2-dimethoxyethane, 1,2-diethoxyethane or anisole; alcohols such as methanol, ethanol, isopropanol or butanol, nitriles such as acetonitrile, propionitrile, n- or isobutyronitrile or benzonitrile; amides such as DMF, DMAC, N-methylformanilide, NMP or hexamethylphosphoramide; sulfoxides such as DMSO or sulfones such as sulfolane, or mixtures of these solvents. Preference is given, to acetonitrile, toluene, xylene, chlorobenzene, n-hexane, cyclohexane or MCH, or mixtures of these solvents; and particular preference, to acetonitrile, THF, toluene or xylene, or mixtures of these solvents.

After the reaction has ended, the solvents are removed and the product is isolated by filtration; or the product is first washed with water and extracted, the organic phase is separated and the solvent is removed under reduced pressure.

The reaction can be accelerated by different catalysts. Preference is given to $FeCl_3$, $FeCl_2$, $FeSO_4$, $CuSO_4$, and $NiCl_2$.

Step D

In step (D) 2-chloro-6-hydroxybenzaldehyde (VII) or its alkaline or alkaline earth metal salt is transformed into 3-chloro-2-(1-hydroxyethyl)phenol (IX) by reacting (VII) with an organometallic reagent of the formula (VIII) and in the presence of a solvent.

Preferred organometallic reagents of the formula (VIII) for this transformation are MeLi, MeMgCl, MeMgBr, MeMgI; most preferred are MeMgCl and MeMgBr.

The amount of organometallic reagents of the formula (VIII) is in the range of 1 to 3 equivalents; preferably 1 to 2 equivalents for 1 equivalent of compounds of the formula (VII).

The temperature during the addition is in the range of 0-100° C., preferably 20-80° C., most preferably 40-70° C.

Suitable solvents for step (D) are for example, aliphatic, alicyclic or aromatic hydrocarbons, for example petroleum ether, n-hexane, n-heptane, cyclohexane, MCH, toluene, xylene or decalin, and ethers such as diethyl ether, diisopropyl ether, MTBE, methyl tert-amyl ether, dioxane, (THF), 2-methyl-THF, 1,2-dimethoxyethane, 1,2-diethoxyethane or anisole or mixtures of solvents. Preference is given to toluene, xylene, n-hexane, cyclohexane, MCH, MTBE, 2-Me-THF, and THF, or mixtures of these solvents and particular preference to THF, 2-Me-THF, toluene or xylene, or mixtures of these solvents.

The reaction of step (D) is usually performed under normal pressure, but can also be performed under reduced or elevated pressure.

Step E

In step (E) 3-chloro-2-(1-hydroxyethyl)phenol (IX) is reacted with compounds of the formula (X) in the presence of a base to give compounds of the formula (I).

Suitable reagents (X) are methansulfonic acid chlorid, methansulfonic acid fluoride-methansulfonic acid anhydride, p-toluenesulfonic acid chloride, benzenesulfonic acid chloride.

The amount of the reagent is between 0.8 to 3.5 equivalents, preferably 1 to 3 equivalents, most preferably 1.2 to 2.5 equivalents for one equivalent of the compound of the formula (IX).

The transformation is performed in the presence of a base. Suitable bases for step (E) are organic bases, for example, triethylamine, ethyl-diisopropylamine, pyridine, 2,6-lutidine, 2-picoline, 3-picoline, 4-picoline, 1,8-diazabicyclo[5.4.0]undec-7-en (DBU), sodium methanolate, sodium acetate, potassium acetate, or potassium-tert-butylate. Suitable inorganic bases are sodium-hydroxide and -carbonate, potassium-hydroxide, -carbonate, calcium-hydroxide and -carbonate. Preference is given to alkali metal carbonate and hydroxide, triethylamine and pyridine.

The amount of base is in the range of 0.5 to 5 equivalents, preferably 1 to 3 equivalents for 1 equivalent of compounds of the formula (IX).

For step (E) a solvent can be used. Suitable solvents are, for example, aliphatic, alicyclic or aromatic hydrocarbons, for example petroleum ether, n-hexane, n-heptane, cyclohexane, MCH, toluene, ortho-xylene, meta-xylene, para-xylene or decalin, and halogenated hydrocarbons, for example chlorobenzene, 1,2-dichlorobenzene, dichloromethane, chloroform, tetrachloromethane, dichloroethane or trichloroethane, ethers such as diethyl ether, diisopropyl ether, MTBE, methyl tert-amyl ether, dioxane, THF, 2-Me-THF, 1,2-dimethoxyethane, 1,2-diethoxyethane or anisole; nitriles such as acetonitrile, propionitrile, n- or isobutyronitrile or benzonitrile; or mixtures of solvents. Preference is given, to toluene, acetonitrile, MTBE, THF, or 2-Me-THF, or mixtures of these solvents.

The reaction of step (E) is done under normal pressure, but can also be performed under reduced or elevated pressure.

After the reaction has ended, the product is first washed with aqueous acid and extracted, the organic layer is separated and the solvent is evaporated under reduced pressure.

It is also possible to transform compound of the formula (IX) into 3-chloro-2-vinylphenol (XII) (Scheme 2, step F) and the formed product (XII) in situ or after isolation into compounds of the formula (I) (Scheme 2, step G).

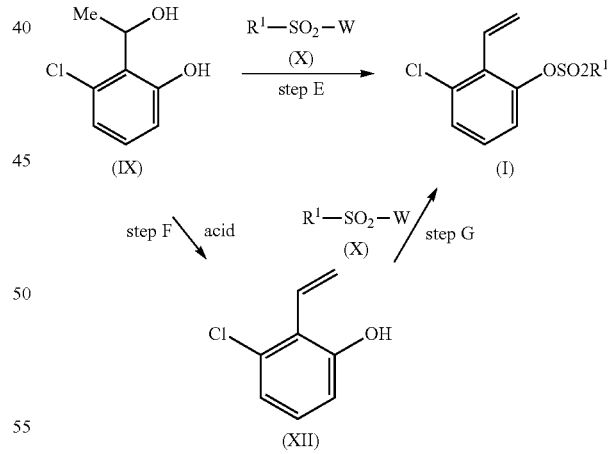

Scheme 2

Step F

In step (F) 3-chloro-2-(1-hydroxyethyl)phenol (IX) is transformed into 3-chloro-2-vinylphenol (XII) in the presence of acid and a solvent.

Suitable organic acids are carboxylic acids such as acetic acid, propionic acid, trifluoroacetic acid, benzoic acid; sulfonic acids such as methansulfonic acid, p-tolylsulfonic acid, trifluoromethansulfonic acid.

Suitable inorganic acids are hydrochloric acid, hydrobromic acid, sulfuric acid, phosphoric acid, sodium bisulfate, and disodium phosphate. Preference is given to methansulfonic acid, trifluoromethansulfonic acid and tolylsulfonic acid.

The amount of acid is in the range of 0.001 to 2 equivalents, preferably 0.01 to 1.5 equivalents, most preferably 0.05 to 1 equivalents for 1 equivalent of compounds of the formula (IX).

Suitable solvents are, for example, aliphatic, alicyclic or aromatic hydrocarbons, for example petroleum ether, n-hexane, n-heptane, cyclohexane, MCH, toluene, xylene or decalin, and halogenated hydrocarbons, for example chlorobenzene, dichlorobenzene, dichloromethane, chloroform, tetrachloromethane, dichloroethane or trichloroethane, ethers such as diethyl ether, diisopropyl ether, MTBE, methyl tert-amyl ether, dioxane, THF, 2-Me-THF, 1,2-dimethoxyethane, 1,2-diethoxyethane or anisole; alcohols such as methanol, ethanol, isopropanol or butanol, nitriles such as acetonitrile, propionitrile, n- or isobutyronitrile or benzonitrile; amides such as DMF, DMAC, N-methylformanilide, NMP or hexamethylphosphoramide; sulfoxides such as DMSO or sulfones such as sulfolane, or mixture of solvents. Preference is given to toluene, xylene, decalin, chlorobenzene, DMF, DMAC, and NMP, or mixtures of these solvents.

The temperature is in the range of 0-200° C., preferably 80-180° C., more preferably 120-170° C.

The reaction of step (F) is done under normal pressure, but can also be performed under reduced or elevated pressure.

Step G

In step (G) 3-chloro-2-vinylphenol (XII) is transformed into compounds of the general formula (I) in the presence of (X) and a base.

Suitable reagents (X) are methansulfonic acid chlorid, methansulfonic acid fluoride-methansulfonic acid anhydride, p-toluenesulfonic acid chloride, benzenesulfonic acid chloride.

The amount of the reagent (X) is between 0.8 to 2 equivalents, preferably 0.8 to 1.8 equivalents, more preferably 0.8 to 1.5 equivalents for one equivalent of the compound of formula (XII).

The transformation is performed in the presence of a base. Suitable bases for step (G) are organic bases, for example, triethylamine, ethyl-diisopropylamine, pyridine, 2,6-lutidine, 2-picoline, 3-picoline, 4-picoline, DBU, sodium methanolate, sodium acetate, potassium acetate, or potassium-tert-butylate. Suitable inorganic bases are sodium-hydroxide and -carbonate, potassium-hydroxide, -carbonate, calcium-hydroxide and -carbonate. Preference is given to alkali metal carbonate, alkali metal hydroxide, triethylamine and pyridine.

The amount of the base is in the range of 0.5 to 2 eq, preferably 0.8 to 1.5 eq. for one eq. of the compound of formula (XII).

Reaction temperature is a range of −20 to +100° C., preferably −10 to +60° C., most preferably −5 to +25° C.

For step (G) a solvent can be used. Suitable solvents are, for example, aliphatic, alicyclic or aromatic hydrocarbons, for example petroleum ether, n-hexane, n-heptane, cyclohexane, MCH, toluene, ortho-xylene, meta-xylene, para-xylene or decalin, and halogenated hydrocarbons, for example chlorobenzene, 1,2-dichlorobenzene, dichloromethane, chloroform, tetrachloromethane, dichloroethane or trichloroethane, ethers such as diethyl ether, diisopropyl ether, MTBE, methyl tert-amyl ether, dioxane, THF, 2-Me-THF, 1,2-dimethoxyethane, 1,2-diethoxyethane or anisole; nitriles such as acetonitrile, propionitrile, n- or isobutyronitrile or benzonitrile; or mixtures of these solvents. Particular preference is given to toluene, acetonitrile, MTBE or THF, or mixtures of these solvents.

The reaction of step (G) is done under normal pressure, but can also be performed under reduced or elevated pressure.

EXPERIMENTAL EXAMPLES

Example 1

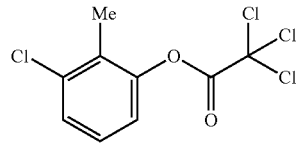 [SMILES: Cc1c(Cl)cccc1OC(=O)C(Cl)(Cl)Cl]

3-Chloro-2-methylphenyl trichloroacetate 142 g of 2-methyl-3-chlorophenol and 90 g of pyridine were placed in 700 ml toluene. 180 g of trichloroacetylchloride were added to this slurry within two h. The mixture was stirred for two h at 20° C. and the precipitate (pyridinium hydrochloride salt) was filtered off. The filtrate was washed two times with 200 ml of cold water and dried over MgSO$_4$. The solvent was removed in vacuum to give 288 g of a yellow liquid (98% yield).

m/z=288

1H-NMR (CDCl$_3$): δ: 7.36 (d, 1H), 7.2 (t, 1 H), 7.08 (d, 1H) ppm.

Example 2

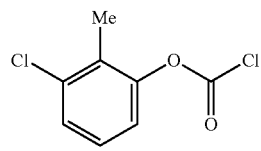 [SMILES: Cc1c(Cl)cccc1OC(=O)Cl]

3-Chloro-2-methylphenyl carbonochloridate 14.2 g of 2-methyl-3-chlorophenol and 14 g of phosgene (as 20% solution in toluene) were charged to the reaction flask. The mixture was cooled to 10° C. and 12.2 g of N,N-dimethylaniline ware added within one hour at this temperature. The mixture was stirred for three hours at room temperature. After that the precipitate was filtered off. The toluene was removed in vacuum and the resulting residue was dissolved in 100 ml methyl-tert.-butylether. The formed new precipitate was filtered off and the filtrate concentrated in vacuum yielding 18.4 g of a pale yellow liquid.

m/z=205

$^1$H-NMR (CDCl$_3$): δ:7.30 (m, 1H), 7.15 (t, 1 H), 7.15 (m, 1H) ppm.

Example 3

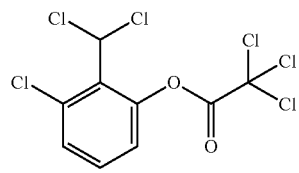 [SMILES: O=C(Oc1cccc(Cl)c1C(Cl)Cl)C(Cl)(Cl)Cl]

3-Chloro-2-(dichloromethyl)phenyl trichloroacetate

A solution of 85 g (0.295 mol) of compound of example 1 in 280 ml carbon tetrachloride was placed in a glass reactor with an inlet pipe for chlorine gas and a dip tube with a UV-lamp (Heraeus TQ-Strahler 150/56001725). The solution was heated to 60° C. and 96 g (1.354 mol) $Cl_2$ were passed into the solution under UV-irridation within 490 minutes. The carbon tetrachloride was distilled off to give 111.6 g of a light yellow oil with a purity of 91.2% (GC), representing a yield of 97% of theory.

GC/MS: m/z=354 ($M^+$, $6\times^{35}Cl$, 18%), 319 (M-Cl, 100%).

$^1$H-NMR (600 MHz, $CDCl_3$): δ=7.2 (m, 1H), 7.3 (s, 1H, Ar—$CH(Cl)_2$), 7.4-7.47 (m, 2H) ppm.

Example 4

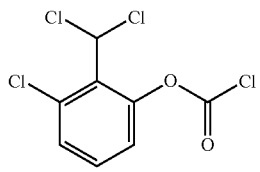 [SMILES: O=C(Cl)Oc1cccc(Cl)c1C(Cl)Cl]

3-Chloro-2-(dichloromethyl)phenyl carbonochloridate

A solution of 4.1 g (20 mmol) of compound of example 2 in 90 ml 2 carbon tetrachloride was placed in a glass reactor with an inlet pipe for chlorine gas and a dip tube with a UV-lamp (Heraeus TQ-Strahler 150/56001725). The solution was heated to 50° C. and 21 g (296 mmol) $Cl_2$ were passed into the solution under UV-irridation within 450 minutes. The carbon tetrachloride was distilled off to give 98% yield of the target compound.

GC/MS: m/z=272 ($M^+$, $4\times^{35}Cl$; 18%), 237 (M-35; 40%), 193 (M-OC(O)Cl; 100%).

$^1$H-NMR ($CDCl_3$): δ=7.3 (m, 1H), 7.38-7.47 (m, 3H) ppm.

Example 5

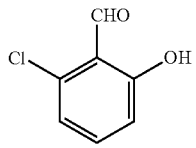

2-Chloro-6-hydroxybenzaldehyde

A mixture 36 g of 3-chloro-2-(dichloromethyl)phenyl trichloroacetate, 30 ml of acetic acid and 100 ml water was heated at 90-95° C. After six hours the mixture was cooled to room temperature and the product was extracted three times each with 50 ml of ethylacetate. The organic extract was washed with 100 ml of water and the solvent removed in vacuum to give 14.8 g of a yellow solid.

m/z=156

$^1$H-NMR ($CDCl_3$): δ:11.5 (s, 1H), 10.4 (s, 1H), 7.5 (t, 1H), 7.1 (d, 1H), 6.9 (s, 1H) ppm.

Example 6

2-Chloro-6-hydroxybenzaldehyde

A mixture of 27 g of 3-chloro-2-(dichloromethyl)phenyl carbonochloridate, 30 ml of acetic acid and 80 ml water was heated at 90-95° C. After four hours the mixture was cooled to room temperature and the product was extracted three times with 50 ml of ethylacetate, each. The organic extract was washed with 100 ml of water and the solvent removed in vacuum to give 14.5 g of a yellow solid $^1$H NMR ($CDCl_3$): δ:11.5 (s, 1H), 10.4 (s, 1H), 7.5 (t, 1H), 7.1 (d, 1H), 6.9 (s. 1H) ppm.

Example 7

2-Chloro-6-hydroxybenzaldehyde

A mixture of 36 g of 3-chloro-2-(dichloromethyl)phenyl trichloroacetate, 30 ml of formic acid and 100 ml water was heated at 90° C. After six hours the mixture was cooled to room temperature and the product was extracted three times with 50 ml of ethylacetate, each. The organic extract was washed with 100 ml of water and the solvent was removed in vacuum to give 14.7 g of a yellow solid.

$^1$H NMR ($CDCl_3$): δ:11.5 (s, 1H), 10.4 (s, 1H), 7.5 (t, 1H), 7.1 (d, 1H), 6.9 (s, 1H) ppm.

Example 8

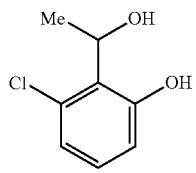 [SMILES: CC(O)c1c(O)cccc1Cl]

3-Chloro-2-(1-hydroxyethyl)phenol

To 500 ml of a 3M THF solution of MeMgCl is added 107 g of a 60° C. warm melt of 2-chloro-6-hydroxybenzaldehyde over 30-60 min. The temperature of the mixture is maintained at reflux during the addition. Gas evolution is observed. After complete addition the mixture was cooled to room temperature and added to 650 ml 10% aqueous HCl under ice cooling. The organic layer is washed with saturated aqueous $NaHCO_3$, dried with $MgSO_4$, filtered and the solvent removed to give 123 g of 3-chloro-2-(1-hydroxyethyl)phenol (91% of theory)

Quant. NMR: 87%

$^1$H NMR (DMSO-d6): δ=10.0 (br s, 1H), 7.1 (t, 1H), 6.9 (d, 1H), 6.7 (s, 1H), 5.28-5.31 (m, 1H), 1.4 (d, 3H) ppm.

Example 9

3-Chloro-2-(1-hydroxyethyl)phenol

To a mixture of 5.8 g of the potassium salt of 2-chloro-6-hydroxybenzaldehyde in 20 g THF was added 10.4 ml of a 3M MeMgCl solution in THF within 30 min at reflux temperature. The HPLC showed 80% conversion.

Example 10

3-Chloro-2-(1-hydroxyethyl)phenol

To a mixture of 1.1 g of the potassium salt of 2-chloro-6-hydroxybenzaldehyde in 9 g THF was added 3.5 ml Methyllithium of a 1.6M solution in ether at 0° C. The HPLC showed 1:3 mixture of product:aldehyde.

Example 11

3-Chloro-2-vinylphenol

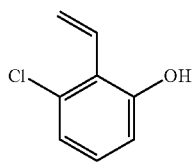

To a solution of 50 g 3-chloro-2-(1-hydroxyethyl)phenol (87% purity) in 280 g DMAc is added 24 g of methansulfonic acid at 160° C. and stirred for 90 min. The mixture is cooled, 250 ml toluene and 200 ml water are added, the organic layer washed with saturated aqueous NaHCO$_3$. The crude product is concentrated via thin film distillation to obtain 3-chloro-2-vinylphenol as a 60 wt-% solution in DMAc (determined by quant. NMR), which corresponds to circa 78% yield.

$^1$H NMR (DMSO-d6): δ=10.1 (s, 1H), 7.06 (t, 1H), 6.90-6.79 (m, 3H), 6.13-6.10 (m, 1H), 5.54-5.51 (m, 1H) ppm.

Example 12

3-Chloro-2-vinylphenol

To a mixture of 16.8 g 3-chloro-2-(1-hydroxyethyl)phenol in DMAC/xylene (27 g/54 g) is added 9.3 g of methansulfonic acid at 160° C. and stirred for 90 min. The mixture is concentrated via thin film distillation to obtain 37.5 g 3-chloro-2-vinylphenol as a solution in DMAC (34% purity determined by quant. NMR), which corresponds to 85% yield.

Example 13

3-Chloro-2-vinylphenol

To a mixture of 17.4 g 3-chloro-2-(1-hydroxyethyl)phenol in 180 g DMAC is added 7.6 g of trifluoromethylsulfonic acid at 160° C. and stirred for 30 min. The mixture is cooled and concentrated via thin film distillation to obtain 35.7 g 3-chloro-2-vinylphenol as a solution in DMAC (34% purity determined by quant. NMR), which corresponds to 77% yield.

Example 14

3-Chloro-2-vinylphenol

To a mixture of 7.4 g 3-chloro-2-(1-hydroxyethyl)phenol in DMAC/toluene (18 g/36 g) is added 4.1 g of methansulfonic acid at 160° C. and stirred for 120 min. The produced water is continuously removed via Dean-Stark apparatus. The mixture is cooled, the organic layer washed with saturated aqueous NaHCO$_3$. The crude product is concentrated to obtain 8.5 g 3-chloro-2-vinylphenol as a 57 wt-% solution in DMAC (determined by quant. NMR), which corresponds to 73% yield.

Example 15

3-Chloro-2-vinylphenol

To a mixture of 1 g 3-chloro-2-(1-hydroxyethyl)phenol in 9 g tetramethylurea is added 0.5 g of methansulfonic acid at 140° C. and stirred for 60 min. HPLC indicates 88% conversion and 82% 3-chloro-2-vinylphenol.

Example 16

3-Chloro-2-vinylphenol

To a mixture of 0.5 g 3-chloro-2-(1-hydroxyethyl)phenol in 4.5 g DMAc is added 0.025 g of methansulfonic acid at 160° C. and stirred for 120 min. HPLC indicates 94% conversion and 77% 3-chloro-2-vinylphenol.

Example 17

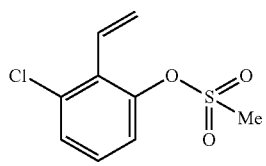

3-Chloro-2-vinylphenyl methanesulfonate

The DMAC solution of example 11 is added to 17 g triethylamine in 400 g MTBE. At 0-5° C. 19.1 g of methansulfonic acid chloride is added within one hour via syringe pump. After stirring for another 10 min the mixture is added to 250 ml of 15% aqueous hydrochloric acid, the organic layer dried over MgSO$_4$ and concentrated in vacuo to give 53 g crude 3-chloro-2-vinylphenyl methanesulfonate (Quant. NMR 82% purity; 95% of theory).

Recrystallization in methylcyclohexane/MTBE gives 34.5 g product (quant. NMR: 96% purity; 72% of theory).

$^1$H NMR (DMSO-d6): δ=7.52-7.51 (m, 1H), 7.44-7.39 (m, 2H), 6.75-6.70 (m, 1H), 5.87-5.84 (m, 1H), 5.76-5.74 (m, 1H), 5.54-5.51 (m, 1H), 3.44 (s, 3H) ppm.

Example 18

3-Chloro-2-vinylphenyl methanesulfonate

To a solution of 2.59 g of 3-chloro-2-(1-hydroxyethyl) phenol and 4.3 g of methansulfonic acid chloride in 50 ml methyl-tert.-butylether 3.79 g of triethylamine was slowly added at 0° C. The mixture was stirred 1 h at 0° C. and 5 h at 20° C. 50 ml of water were added to the formed suspension and the organic phase was separated and washed with 50 ml water. The solvent was evaporated and the product was purified via crystallization from the mixture MCH/MTBE yielding 2.64 g (76%) of the white solid.

$^1$H NMR (DMSO-d6): δ=7.52-7.51 (m, 1H), 7.44-7.39 (m, 2H), 6.75-6.70 (m, 1H), 5.87-5.84 (m, 1H), 5.76-5.74 (m, 1H), 5.54-5.51 (m, 1H), 3.44 (s, 3H) ppm.

The invention claimed is:

1. A process for preparing one or more 3-chloro-2-vinylphenylsulfonate derivatives of formula (I),

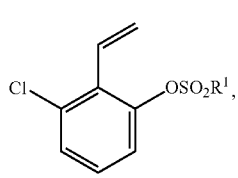

(I)

wherein
R¹ represents $C_1$-$C_6$-alkyl, phenyl, 4-methylphenyl or benzyl,
comprising
(A) reacting 3-chloro-2-methylphenol of formula (II)

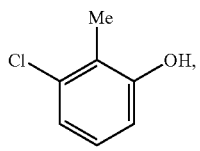
(II)

with a compound of formula (III),

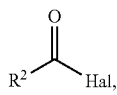
(III)

wherein
Hal represents F or Cl and
R² represents F, Cl, $F_3C$, $F_2HC$, $Cl_3C$, $Cl_2HC$, $ClH_2C$ or $Cl_3CO$,
or reacting the 3-chloro-2-methylphenol of formula (II)
with an acid derivative of formula (IV),

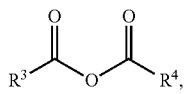
(IV)

wherein
R³ and R⁴ independently from each other represent $F_3C$, $F_2HC$, $Cl_3C$, $Cl_2HC$, or $ClH_2C$,
or reacting the 3-chloro-2-methylphenol of formula (II)
with triphosgene
in the presence of a base and a solvent
to form a compound of formula (V)

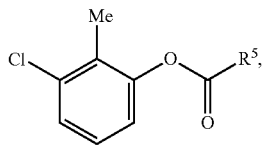
(V)

wherein
R⁵ represents F, Cl, $CCl_3$, $CHCl_2$, $CH_2Cl$, $CF_3$, $CHF_2$ or 3-chloro-2-methylphenoxy;
(B) reacting one or more compounds of formula (V) with a chlorinating agent to produce one or more compounds of formula (VI)

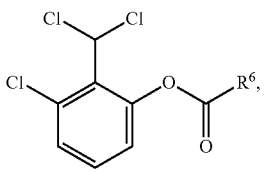
(VI)

wherein
R⁶ represents F, Cl, $CCl_3$, $CHCl_2$, $CH_2Cl$, $CF_3$, $CHF_2$ or 3-chloro-2-(dichloromethyl)phenoxy;
(C) reacting the compound of formula (VI) under acidic conditions or at elevated temperature in water to produce 2-chloro-6-hydroxybenzaldehyde (VII)

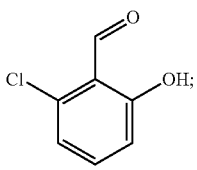
(VII)

(D) reacting the compound of formula (VII) or an alkaline or alkaline earth metal salt thereof in the presence of a solvent with a compound of formula (VIII)

Me-Q (VIII), wherein
Q represents Li, Na, K, MgCl, MgBr or, MgI
to produce 3-chloro-2-(1-hydroxyethyl)phenol (IX)

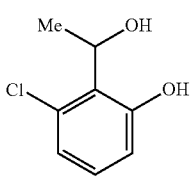
(IX)

and
(E) forming 3-chloro-2-vinylphenylsulfonate derivatives of formula (I) by reacting the compound of formula (IX) in the presence of a base with a compound of formula (X)

R¹—$SO_2$—W (X), wherein
W represents F, Cl, Br or $OSO_2R^1$.
2. The process according to claim 1, wherein
R¹ represents methyl, ethyl, n-propyl, i-propyl, n-butyl, phenyl, 4-methylphenyl or benzyl;
R² represents F, Cl, $F_3C$, $F_2HC$, $Cl_3C$, $Cl_2HC$, $ClH_2C$ or $Cl_3CO$;
R³ and R⁴ independently from each other represent $F_3C$, $F_2HC$, $Cl_3C$, $Cl_2HC$ or $ClH_2C$;
R⁵ represents F, Cl, $CCl_3$, $CHCl_2$, $CH_2Cl$, $CF_3$, $CHF_2$ or 3-chloro-2-methylphenoxy;
R⁶ represents F, Cl, $CCl_3$, $CHCl_2$, $CH_2Cl$, $CF_3$, $CHF_2$ or 3-chloro-2-(dichloromethyl) phenoxy;
W represents F, Cl or $OSO_2R^1$; and
Q represents Na, K, MgCl or MgBr.

3. The process according to claim 1, wherein $R^1$ represents methyl, ethyl, n-propyl, phenyl, or 4-methylphenyl;

$R^2$ represents F, Cl, $F_3C$, $F_2HC$, $Cl_3C$, $Cl_2HC$, $ClH_2C$ or $Cl_3CO$;

$R^3$ and $R^4$ independently from each other represent $F_3C$, $Cl_3C$, $Cl_2HC$, or $ClH_2C$;

$R^5$ represents F, Cl, $CCl_3$, $CHCl_2$, $CH_2Cl$, $CF_3$, $F_2HC$ or 3-chloro-2-methylphenoxy;

$R^6$ represents F, Cl, $CCl_3$, $CHCl_2$, $CH_2Cl$, $CF_3$, $F_2HC$ or 3-chloro-2-(dichloro)methylphenoxy;

W represents F, Cl or $OSO_2R^1$; and

Q represents Na, K, MgCl or MgBr.

4. The process according to claim 1, wherein $R^1$ represents methyl or 4-methylphenyl;

$R^2$ represents F, Cl, $F_3C$ or $Cl_3CO$;

$R^3$ and $R^4$ independently from each other represent $F_3C$ or $Cl_3C$;

$R^5$ represents F, Cl, $CCl_3$, $F_3C$ or 3-chloro-2-methylphenoxy;

$R^6$ represents F, Cl, $CCl_3$, $F_3C$ or 3-chloro-2-(dichloro)methylphenoxy;

W represents F, Cl or $OSO_2R_1$; and

Q represents MgCl or MgBr.

5. The process according to claim 1, wherein in (A), 3-methylpyridine and 2-methyl-5-ethylpyridine are used as base and dichloromethane, toluene, chlorobenzene or dichloromethane as solvent.

6. The process according to claim 1, wherein in (B), chlorine is used as chlorinating agent.

7. The process according to claim 1, wherein in (C), HCOOH, $CH_3COOH$, $H_2SO_4$, or HCl is used as acid.

8. The process according to claim 1, wherein (C) is performed in water at temperatures between 80° C. and 140° C.

9. The process according to claim 1, wherein in (D), MeMgCl or MeMgBr is used as organometallic reagent and THF, 2-Me-THF, toluene or xylene as solvent.

10. The process according to claim 1 wherein in (E), alkali metal carbonate or hydroxide, triethylamine or pyridine is used as base.

11. The process for preparing one or more 3-chloro-2-vinylphenylsulfonate derivatives of formula (I),

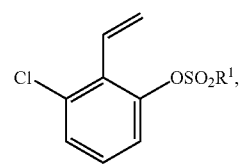

according to claim 1 further comprising (F) transforming one or more compounds of formula (IX) into 3-chloro-2-vinylphenol of formula (XII)

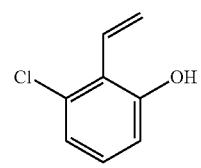

in the presence of an acid and a solvent and (G) transforming 3-chloro-2-vinylphenol of formula (XII) into a 3-chloro-2-vinylphenylsulfonate derivative of formula (I) in the presence of one or more compounds of formula (X) and a base.

12. The process according to claim 1, comprising reacting the 3-chloro-2-methylphenol of formula (II) with the compound of formula (III).

13. The process according to claim 1, comprising reacting the 3-chloro-2-methylphenol of formula (II) with the acid derivative of formula (IV).

14. The process according to claim 1, comprising reacting the 3-chloro-2-methylphenol of formula (II) with triphosgene.

15. A compound of formula (V)

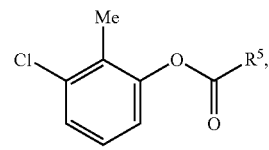

wherein $R^5$ represents F, Cl, $CCl_3$, $CHCl_2$, $CH_2Cl$, $CF_3$, $CHF_2$ or 3-chloro-2-methylphenoxy.

* * * * *